United States Patent
Franks

[19]

[11] Patent Number: 5,958,388
[45] Date of Patent: Sep. 28, 1999

[54] MATERIAL AND METHOD FOR REMOVING SEBUM FROM HUMAN SKIN

[76] Inventor: James W. Franks, 2153 Driftwood Cir., Palm Beach Gardens, Fla. 33410

[21] Appl. No.: 08/960,472

[22] Filed: Oct. 29, 1997

[51] Int. Cl.[6] .......................... A61K 7/48; A61K 47/02; A61K 47/32
[52] U.S. Cl. .......................... 424/69; 514/844; 510/130
[58] Field of Search .......................... 424/401, 69, 489, 424/501; 514/844; 510/130, 157

[56] References Cited

U.S. PATENT DOCUMENTS

| 4,000,317 | 12/1976 | Menda et al. . |
|---|---|---|
| 4,035,267 | 7/1977 | Gleckler et al. . |
| 4,246,257 | 1/1981 | Elliott et al. . |
| 4,885,109 | 12/1989 | Umemoto et al. . |
| 4,957,747 | 9/1990 | Stiefel . |
| 5,023,075 | 6/1991 | Macchio et al. . |
| 5,030,446 | 7/1991 | Russ et al. . |
| 5,145,685 | 9/1992 | Carmody . |

*Primary Examiner*—Edward J. Webman

[57] ABSTRACT

A material in powder form having a plurality of particles containing alumina trihydrate and polymethyl methacrylate, and a method of using same to remove sebum from human skin.

8 Claims, 1 Drawing Sheet

MATERIAL AND METHOD FOR REMOVING SEBUM FROM HUMAN SKIN

DESCRIPTION

1. Technical Field

This invention relates to skin care, and more specifically to a method of removing oil, such as sebum, from the skin without the use of soap.

2. Background Art

Human skin produces two types of oil: epidermal oil and sebum. Epidermal oil is produced inside every healthy skin cell. Our skin cells are constantly dividing and multiplying, producing new cells which slowly mature and migrate toward the surface, where they produce a tough protein called "keratin". Cells full of keratin ultimately die, but remain attached to adjacent skin cells to form a strong protective outer layer. In the process of maturing, the skin cells are also producing progressively thicker and thicker oils.

The older, dead keratin cells are rich in "epidermal lipids". As used herein, the term "epidermal lipids" refers to the naturally occurring waxes, semi-solid triglycerides, and solid sterols (such as cholesterol) which have little or no tendency to exit skin cells and flow across the surface of a person's skin at normal body skin temperatures. When the mature skin cells die, these epidermal lipids, reinforced by the strands of keratin protein, form a protective barrier against many chemicals and toxins which might otherwise attack the living skin cells immediately below the epidermis.

Living, mature skin cells do not have minute pores for excreting epidermal oils. They do, however, have the ability to actively express microscopic, lipid enriched, globules called "lamellae" into the interstices between adjacent cells. These lipid laden globules, which are covered with cellular material, fill the spaces between epidermal cells like mortar between bricks and contribute to the integrity of skin. Together, the keratin reinforced epidermal lipid barrier and the lamellae form a protective shield which allows our skin to contact noxious materials such as mineral spirits or freshly cut onions without absorbing these noxious materials through this protective shield. Normal skin has adequate amounts of epidermal lipids and lamellae and is therefore unaffected by day-to-day contact with such noxious materials, because the keratin, epidermal lipids, and lamellae prevent these irritants from penetrating into the skin. As a result, we experience no stinging, burning or toxicity from such contact.

The second oil produced by human skin is sebum, which is the product of the sebaceous gland. Every pore and every hair follicle on the human body has an associated sebaceous gland that produces sebum. The sebaceous glands in the scalp, forehead and upper back are the most densely clustered and productive of the sebaceous glands. Sebum differs from epidermal oil in two important respects: where it is found, and what it is made of. First, sebaceous glands are located below the skin, but they excrete all of the sebum through large pores that extend up to the surface of the skin. Second, the product of each sebaceous gland is a mixture of waxes, sterol precursors, triglycerides and other compounds that form a liquid, sebum, that fills the pore and flows out onto the above epidermis. Beginning at puberty, sebaceous glands continually produce relatively large amounts of sebum, and because sebum has low viscosity at normal skin temperature, the sebum tends to spread across the surface of the skin and produces a sheen that is generally considered unattractive.

The most common way to eliminate this sheen is to wash the surface of the skin with soap and water. Soap easily dissolves sebum on the surface of the skin, but it also dissolves and washes away a portion of the epidermal lipids that have conbined with the keratin to form our epidermal lipid barrier. For most people, if washing is done only once or twice a day few, if any, problems occur. However, more frequent washing, or using a wash cloth, cotton swab, or gritty cleanser with soap and water can result in microscopic tearing of the keratin reinforced epidermal lipid barrier and ripping away of the cellular material that surrounds the lipid globules in the lamellae. The soap is then able to dissolve and wash away the epidermal lipids in the keratin reinforced epidermal lipid barrier and the lipid globules in the lamellae. The result is that much of the protective shield is removed, leaving healthy skin cells exposed and irritated and over-dried by the soap. Unfortunately, sebaceous glands are so active in adults that the sebum is usually replaced in a matter of hours, causing many individuals to continue to assault their skin with further washing. By contrast, the keratin reinforced epidermal lipid barrier and lamellae take days to be replaced, and therefore such an assault eventually causes a weakening of the integrity and barrier function of the epidermis.

What is needed is a material and method for removing excess oil from human skin while avoiding the problems associated with oil removal materials and methods of the prior art.

SUMMARY OF THE INVENTION

It is therefore an object of the present invention to provide a material for removing sebum from human skin.

Another object of the present invention is to use a material to remove sebum from human skin which material does not irritate the skin.

Another object of the present invention is to provide a method of using a material for removing sebum from human skin which method can be repeated with sufficient frequency to control the accumulation of sebum without irritating the skin.

Another object of the present invention is to provide a method of using a material for removing sebum from human skin which leaves epidermal lipids undisturbed and prevents the irritating effects caused by overdrying of the skin.

Another object of the present invention is to provide a material for removing sebum from human skin which rinses off the skin without the use of soap or vigorous rubbing.

Another object of the present invention is to provide a method of using a material to remove sebum from human skin which does not cause damage to the lamellae between healthy skin cells.

According to the present invention, a material in powder form is disclosed which as a plurality of particles containing polymethyl methacrylate and alumina trihydrate, and a method of using such material to remove sebum from human skin is likewise disclosed wherein the powder is placed onto human skin, absorbs sebum, and is rinsed away with water and without the use of soap or vigorous rubbing.

The foregoing and other features and advantages of the present invention will become more apparent from the following description and accompanying photomicrograph.

BEST MODE FOR CARRYING OUT THE INVENTION

Figure 1:
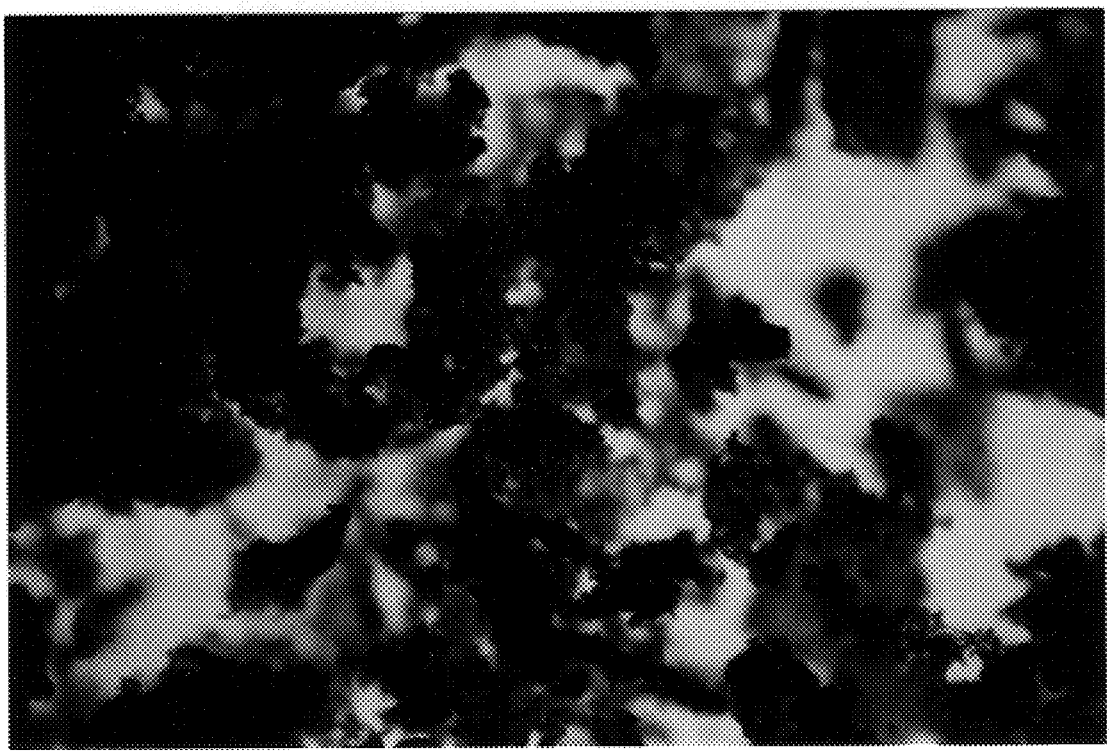
FIG. 1 is a photomicrograph of a sample of the material that it used in the method of the present invention.

FIG. 1 shows a photomicrograph, magnified 100 times, of a sample of the facial powder material that is used in the method of the present invention. The present invention is made from two ingredients: an acrylic, poly-methyl methacrylate (hereinafter referred to as "PM"), and alumina trihydrate (hereinafter referred to as a "AT"). When mixed together at high temperature, the molten acrylic and alumina trihydrate combine to form a tough, rock-like substance (hereinafter referred to as "PMAT") that can be cast into various shapes. PMAT containing, by weight, less than 70% alumina trihydrate and more than 30% polymethyl methacrylate is sold commercially under the name CORIAN, a registered trademark of the DuPont Corporation of Wilmington, Del. CORIAN is considered to be non-porous, and has found wide acceptance for use in kitchen counter tops, sinks, and an endless array of smaller products from salt shakers to ink pens.

While the such uses of PMAT are well known, the inventor has discovered another beneficial product that can be produced from PMAT: facial powder. The inventor has discovered that when pieces of PMAT are ground and filtered into a fine powder, the powder can be used to remove sebum from human skin without producing the skin irritation that results from frequent washing with soap and water.

Since PMAT in the form of CORIAN is readily available, the inventor ground CORIAN to produce the powder which is used in the present invention. The ground CORIAN was then filtered through stainless steel wire mesh having a count of 80×80 wires per square inch. The wire mesh was made of a first set of 0.0055 inch diameter wires spaced 0.0070 inches apart, and a second set of 0.0055 inch diameter wires spaced 0.0070 inches apart, and the second set of wires were woven into the first set perpendicular to the wires of the first set to form a wire cloth having openings that measured 0.0070 inches by 0.0070 inches. As those skilled in the art will readily appreciate, sifting ground PMAT through mesh having 0.0070 inch by 0.0070 inch openings produces PMAT particles having a girth of not more than 0.028 inch (0.0070 inch×4), and an indeterminate height. After trying wire cloth mesh of differing opening sizes, the inventor concluded that particles having a girth of 0.028 or less were desirable because they formed a smooth powder, whereas larger girth sizes allowed larger particles that seemed to be too gritty to be used as a facial powder.

As FIG. 1 shows, the product of the filtering process is PMAT "flakes" which, unlike the slabs of CORIAN from which they were produced, appear to be very porous, having a multitude of interstitial voids. Additionally, each flake is very irregular in shape, resulting in a very large surface area relative its size and weight, as compared to the original slab of CORIAN from which it was produced. The inventor believes that in this ground and filtered form, the flakes of PMAT may absorb sebum from the skin by a capillary action similar to that by which a paper towel absorbs water.

As those skilled in the art will readily appreciate, if a paper towel is laid onto a small puddle of water on a tabletop, the paper towel will absorb most, but not all of the water. If the paper towel is then lifted off the tabletop without wiping, a thin layer of water will be left on the tabletop. Similarly, when flakes of ground and filtered PMAT are placed onto a sebum rich portion of human skin, such as on the face, with a make-up brush, the powder flakes absorb most, but not all of the sebum. The non-liquid epidermal lipids of the keratin reinforced epidermal lipid barrier and the cellular material encased lamellae are essentially unaffected by the powder flakes because the powder is laid onto the skin instead of being scrubbed into the skin. As a result, the keratin reinforced epidermal lipid barrier and the lamellae remain intact, while the sebum flows into the interstices of the PMAT flakes and becomes entrapped therein. Since the epidermal lipids of the keratin reinforced epidermal lipid barrier are non-liquid at normal body skin temperature, these lipids do not flow into the interstices of the PMAT flakes.

In addition, since the powder flakes are laid onto the surface of the skin, as opposed to being scrubbed into it, the cellular material surrounding the lipids in the lamellae remains intact, and the lamellae is unaffected by the PMAT flakes. When the powder is washed off of the skin using only water, the powder leaves the skin taking the sebum therein with powder. As a result, the excess sebum is removed from the skin, providing an sebum-free appearance, but the keratin reinforced epidermal lipid barrier and the lamellae remain along with a very thin layer of sebum, maintaining the integrity of the skin's barrier while providing the luster that is associated with clean, healthy skin.

During initial testing, PMAT facial powder having a girth of less than 0.028 inch, produced as described above, was applied to the facial skin of several volunteers using a common cosmetic powder brush. The PMAT powder was left on the skin for a predetermined period of time, and then removed by rinsing by placing the skin under flowing water. For one portion of the testing, the facial powder was rinsed off with water after five minutes, while in another portion of the testing, the powder was left on all day and rinsed off approximately 12 hours later.

In each portion of the testing, the sebum was quickly absorbed by the PMAT powder yielding an sebum-free appearance. None of the volunteers indicated any significant skin irritation, even when the PMAT powder remained on the facial skin all day; the sebum absorbing properties of PMAT powder lasted the entire day, and resulted in a continual sebum-free appearance. Several weeks of testing confirmed the effectiveness of ground and filtered PMAT as a facial powder, and the fact that the use of the PMAT powder day after day, week after week, causes no apparent skin irritation.

The inventor believes that facial powder made from PMAT does an equal or better job of removing excess skin sebum than does soap and water. It absorbs sebum, and can be rinsed off using plain water. Even prolonged contact with ground and filtered PMAT facial powder, day after day, week after week, causes no apparent skin irritation, yet provides the benefits of an sebum-free appearance without the potential irritation that typically results from the use of soap and water.

Due to its commercial availability, the inventor used the CORIAN form of PMAT in the current invention. However, the inventor believes that PMAT containing 30% or less polymethyl methacrylate would also be effective at removing the sebum, although a different amount of such PMAT facial powder may be necessary to remove the same amount of sebaceous sebum. Specifically, the inventor believes that the effectiveness of PMAT at removing sebum is directly related to the ratio of alumina trihydrate to polymethyl methacrylate, and that through further testing by varying this ratio an optimum ratio can be determined which absorbs the greatest amount of sebum in the least amount of time.

Although this invention has been shown and described with respect to detailed embodiments thereof, it will be understood by those skilled in the art that various changes in form and detail thereof may be made without departing from the spirit and scope of the claimed invention.

I claim:

1. A method of removing sebum from skin, said method comprising:

providing a powder having a plurality of particles, each of said particles containing alumina trihydrate and polymethyl methacrylate, said particles containing, by weight, less than 70% alumina trihydrate and more than 30% polymethyl methacrylate;

placing said powder into contact with sebum located on human skin;

leaving said powder in contact with said sebum for a predetermined period of time to allow said powder to absorb a portion of said sebum; and removing said powder and said portion of sebum absorbed therein from said skin.

2. The method of claim 1 wherein the predetermined period of time is at least one minute.

3. The method of claim 1 wherein the predetermined period of time is at least one minute.

4. A method of removing sebum from skin, said method comprising:

providing a powder having a plurality of particles, each of said particles containing alumina trihydrate and polymethyl methacrylate, placing said powder into contact with sebum located on human skin, said skin having lamellae containing lipids located therein, leaving said powder in contact with said sebum for a predetermined period of time to allow said powder to absorb a portion of said sebum, and removing said powder and said portion of sebum absorbed therein from said skin.

5. The method of claim 4 wherein the predetermined period of time is at least one minute.

6. The method of claim 4 wherein said portion does not include said lipids.

7. The method of claim 6 wherein the girth of said particles is less than 0.028 inches.

8. The method of claim 7 wherein the predetermined period of time is at least one minute.

* * * * *